United States Patent [19]
Schindler et al.

[11] Patent Number: 6,166,023
[45] Date of Patent: Dec. 26, 2000

[54] 1,5- AND 3-O-SUBSTITUTED 1H-INDAZOLES HAVING ANTI-ASTHMATIC, ANTI-ALLERGIC, ANTI-INFLAMMATORY, IMMUNOMODULATING AND NEUROPROTECTIVE ACTION, PROCESS FOR THEIR PREPARATION AND THEIR USE AS MEDICAMENTS

[75] Inventors: Rudolf Schindler, Dresden; Norbert Höfgen, Medingen; Hildegard Poppe, Dresden; Kay Brune, Marloffstein, all of Germany

[73] Assignee: Arzneimittelwerk Dresden GmbH, Germany

[21] Appl. No.: 09/305,601

[22] Filed: May 5, 1999

[30] Foreign Application Priority Data

May 11, 1998 [DE] Germany ............ 198 21 002

[51] Int. Cl.[7] .................. A61K 31/513; A61K 31/4709; C07D 231/56
[52] U.S. Cl. .......................... 514/258; 514/312; 514/364; 514/365; 514/418; 544/270; 546/158; 548/131; 548/204; 548/361.5
[58] Field of Search .................. 548/361.5, 131, 548/204; 514/418, 364, 365, 312, 258; 544/270; 546/158

[56] References Cited

U.S. PATENT DOCUMENTS

| | | | |
|---|---|---|---|
| 3,318,905 | 5/1967 | Palazzo | 260/310 |
| 3,470,194 | 9/1969 | Palazzo | 260/299 |
| 3,470,298 | 9/1969 | Palazzo | 424/273 |
| 3,966,761 | 6/1976 | Podesva et al. | 260/310 |
| 4,537,966 | 8/1985 | Murray | 546/120 |
| 5,030,643 | 7/1991 | Bernstein et al. | 514/373 |
| 5,776,932 | 7/1998 | Schindler et al. | 514/235.2 |

FOREIGN PATENT DOCUMENTS

| | | |
|---|---|---|
| 191520 | 8/1986 | European Pat. Off. . |
| 19610882 | 9/1997 | Germany . |
| WO 96/04266 | 9/1997 | WIPO . |
| WO 97/34874 | 9/1997 | WIPO . |

OTHER PUBLICATIONS

CA 128, No. 18, 1998 No. 213393d.
CA 129, No. 9, 1998 No. 113513y.
Von Kleemann et al., Pharmazeutische Wirkstoffe, Georg Thieme Publ., 1978, pp. 48–49.
V. J. Aran et al:,Analogues of Cytotstatic, etc., Liebigs Ann. 1996. 683–691.
G. Palazzo, et al., Synthesis and Phamacological, etc., vol. 9, Jan. 1966 pp. 38–41.
R. Schindler et al., 1,5–disubstituted Indazol, etc., Arch. Pharm. Med. Chem., 331, 13–21 (1998).

Primary Examiner—Cecilia Tsang
Assistant Examiner—Sonya N. Wright
Attorney, Agent, or Firm—Gabriel P. Katona L.L.P.

[57] ABSTRACT

The invention relates to 1,5- and 3-O-substituted 1H-indazoles of formula (I)

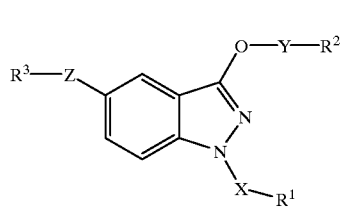

(I)

11 Claims, No Drawings

1,5- AND 3-O-SUBSTITUTED 1H-INDAZOLES HAVING ANTI-ASTHMATIC, ANTI-ALLERGIC, ANTI-INFLAMMATORY, IMMUNOMODULATING AND NEUROPROTECTIVE ACTION, PROCESS FOR THEIR PREPARATION AND THEIR USE AS MEDICAMENTS

TECHNICAL FIELD

The invention relates to the preparation and use of novel derivatives of indazol-3-ol as medicaments having anti-asthmatic, anti-allergic, anti-inflammatory, immunonodulating and neuroprotective properties.

PRIOR ART

Cyclosporin A (CsA) or FK 506 are immunosuppressant natural substances originating from fungi, which inhibit the $Ca^{2+}$-dependent signal transmission pathway in some cell types. In T cells, both compounds inhibit the transcription of a number of genes. CsA and FK506 both bind with high affinity to soluble receptor proteins such as, for example, cyclophilin (Cyp) or Ft-506 binding protein (FKBP) (G. Fischer et al., Nature 337 (1989), 476–478; MW. Harding et al., Nature 341 (1989), 755–760). Both proteins catalyse the isomerization of cis- and trans-amide bond rotamases of eptides and are also often designated as munophilins.

The complex of CsA-Cyp or FR 506-FKBP binds calcineurin (CN) and inhibits its phosphatase activity. The cytosolic, phosphorylating component of the transcription factor NF-AT was recognized as a cellular target molecule of CN, so that in the absence of CN activity the active transcription complex on the IL 2 promoter cannot be switched on (M. K. Rosen, S. L. Schreiber, Angew. Chem. 104 (1992), 413–430; G. Fischer, Angew. Chem. 106 (1994), 1479–1501).

The allergic, asthmatic diseases are based on an inflammatory reaction which is controlled by T cells and their mediators. Corticosteroids are still the agent of choice in the treatment of many allergic diseases. CsA and FK 506 also proved to be a favourable therapeutic in bronchial asthma and underlying inflammations both in animal experiments and in clinical studies.

Despite the large number of attempts at the identification of new active immunophilin inhibitors, until now it was not possible to prepare or isolate any more active structures than CsA, FK 506, rapamycin or derivatives of these natural substances. The high inhibitory potential of CsA, FK 506 and rapamycin, however, is very considerably reduced by the various side effects, in particular the renal toxicity and neurotoxicity (N. H. Sigal et al., J. Exp. Med. 173 (1991), 619–6128). What is behind this fact is the non-specificity of the interaction between immunophilin ligands and the cell-specific binding proteins. As a result, the known medicinal-therapeutic action of these immunosuppressants is considerably restricted. Furthermore, the lacking selectivity of the compounds proves to be problematic especially in long-term therapy.

Substances which inhibit the activity of peptidylprolyl isomerases (PPIases) such as Cyp or FKBF, have neuroprotective properties, stimulate neuronal growth and are suitable for the treatment of neurodegenerative diseases (WO 96/40140, U.S. Pat. No. 5,696,135, WO 97/18828).

Substituted indazole derivatives are known which, however, differ from the claimed compounds with respect to the substituents X, Y, Z, $R^1$, $R^2$ and $R^3$ and their pharmacodynamic action.

Corsi [Boll. Chim. Farm. 111, 566–572 (1972)] and Giannangeli et al. [Boll. Chim. Farm. 121, 465–474 (1982)] reported on the synthesis of 5-hydroxybendazac and EP-A-0 191 520 describes the use of (1-benzyl-5 hydroxy-1H-indazol-3-yl)acetic acid for the treatment of colds.

Baiocchi et al. [Synthesis 1978 (9), 633–648] give a general survey of syntheses and properties of the 1H-indazol-3-ols.

WO 97/34874 describes 1,3,5-trisubstituted indazoles having anti-asthmatic, anti-allergic, anti-inflammatory and immunomodulating action.

WO 96/04266 includes, inter alia, (1H-indazol-3-yloxy)-acetamides substituted by basic radicals and their anti-asthmatic, anti-allergic, anti-inflammatory and immunomodulating properties.

Pfannstiel et al. [Ber. Dtsch. Chem. Ges. 75 (9), 1096–1107 (1942)] reported on the preparation of nitro-1H-indazol-3-ols.

Ketami et al. [J. Heterocycl. Chem. 7 (4), 807–813 (1970)] describe the anti-inflammatory action of the 1,5-disubstituted 3-hydroxy-1H-indazoles.

Hannig et al. [Pharmazie, 30 (11), 706–708] describe 1-benzylated (indazol-3-yl)acylaminocarboxanilides.

JP 48026760 includes, inter alia, 1-benzyl-1H-indazol-3-yloxyacetamides.

EP-A-0 290 145 comprises 1,3,6-trisubstituted indazoles, which are leukotriene antagonists.

U.S. Pat. No. 3,470,194, Pallazo et al. [J. Med. Chem. 9, 38–41 (1966)] and Guyla et al. [Acta pharm. Hung. 44, 49–57 (1974)] describe 1,5-disubstituted (indazol-3-yl)oxy-alkanoic acids and their anti-inflammatory activity.

Klicnar [Coll. Czech. Chem. Comm. 42, 327–337 (1977)] reports on physical data of the acylindazoles.

Yamaguchi et al. [Chem. Pharm. Bull. 43 (2), 332–334 (1995)] describes 3-O-substituted (1-pyridin-3-yl)-indazoles and their anti-asthmatic action.

EP 0 448 206 comprises 1,3,6-trisubstituted indazoles and their use as herbicides, only OH or O-alkyl being permitted in the 3-position.

EP 0 191 520 describes (1-phenylmethyl)-5-hydroxy-1H-indazol-3-yl)oxyacetic acid and its pharmaceutical use.

EP 0 199 543 describes indazoles and other heterocycles having acidic substituents in the radical M as leukotriene antagonists.

U.S. Pat. No. 3,966,761 includes trisubstituted aminoindazoles and their anti-inflammatory and analgesic effects.

U.S. Pat. No. 3,318,905 describes 3-dialkylaminoalkyloxyindazoles having analgesic and anti-inflammatory activity.

K. v. Auwers [Ber. Dtsch. Chem. Ges. 58, 2081–2088 (1925)] describes the constitution of acylindazoles.

Zoni et al. [Il Farmaco Ed. Sci. 23 (5), 490–501 (1968)] and Zoni et al. [Boll. Chim. Farm. 107, 598–605 (1968)] describe the alkylation of 1-substituted 1H-indazol-3-ols.

Evans et al. [Tetrahedron 21, 3351–3361 (1965)] describe the synthesis of 1,3-substituted acyl- and tosylindazoles.

Anderson et al. [J. Chem. Soc. C, 3313–3314 (1971)] describe 1,3-substituted tosylindazoles.

Schmutz et al. [Helv. Chim. Acta 47, 1986–1996 (1964)] describe the alkylation of indazolones.

On account of numerous side effects of the preparations introduced, lack of curative effects and the hitherto too non-specific therapy, a great need for compounds having a high effectiveness and safety furthermore exists for the treatment of asthmatic diseases.

The invention is based on the object of finding new compounds having rotamase-inhibiting and/or pulmonary eosinophil infiltration-inhibiting properties and making them available by targeted synthesis. A completely novel class of substance, which surprisingly binds immunophilins specifically, is represented by the compounds of the formula I according to the invention. This class of compounds has a high affinity for immunophilins such as CypB.

DESCRIPTION OF THE INVENTION

Surprisingly, it has now been found that the new indazole derivatives are able to inhibit the action of PPIase. Accordingly, these compounds are of great importance for the production of medicaments where the inhibition of PPIase is of benefit. Such illnesses are, for example: peripheral neuropathies, neuro-degeneration, stroke, Parkinson's and Alzheimer's diseases, traumatic brain diseases, multiple sclerosis. It has furthermore been demonstrated that the compounds according to the invention are able to inhibit the infiltration of eosinophilic granulocytes into the tissue, which is characteristic of the asthmatic late-phase reaction.

The invention relates to new 1,5- and 3-O-substituted 1H-indazoles of the general formula I Formula I

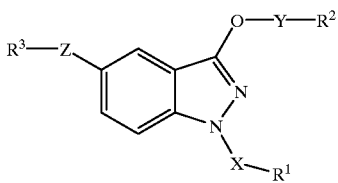

in which X, Y, Z, $R^1$, $R^2$ and $R^3$ have the following meaning:

X can be $-SO_2-$, $-SO-$, $-(CH_2)_p-$, $-(CH_2)_p-O-$, $-(CH_2)_p-(C=O)-$, $-(CH_2)_p-(C=O)-NH-$, $-(CH_2)_p-CHOH-$, $-CHOH-(CH_2)_p-$, $-(CH_2)_p-CH=CH-$, $-CH=CH-(CH_2)_p-$ where p=1 . . . 4, Y can be $-(CH_2)_p-$, $-(CH_2)_p-O-$, $-(CH_2)_p-(C=O)-$, $-(CH_2)_p-(C=O)-NH-$, $-(CH2)_p-(C=O)-NH-(CH_2)_p-$, $-(CH_2)_p-CHOH-$, $-CHOH-(CH_2)_p-$, $-(CH_2)_p-CH=CH-$, $-CH=CH-(CH_2)_p-$ where p=1 . . . 4, Z can be $-O-$, $-S-$, $-SO-$, $-SO_2-$, $-O-(CH_2)p-$ where p=1 . . . 4, $-NH-$, $-NH-(C=O)-$, $-NH-(C=O)-NH-$, $-NH-(C=O)-O-$, $-NH-CH_2-(C=O)-$ and $-NH-(C=O)-CH_2-$, $R^1$, $R^2$ and $R^3$ can be identical or different and have the following meaning:

mono-, bi- or tricyclic saturated or mono- or polyunsaturated carbocycles having 5 . . . 14 ring members, in particular phenyl, naphthyl, anthranyl, fluorenyl; or mono-, bi- or tricyclic saturated or mono- or polyunsaturated heterocycles having 5 . . . 15 ring members and 1 . . . 6 heteroatoms, which are preferably N, O and S, in particular thiophenyl, pyridinyl, isoxazolyl, benzimidazolyl, benzo[1,3] dioxolyl, pyrimidinyl, quinolyl, quinazolinyl, morpholinyl, pyrrolidinyl, pyrrolyl, benz[1,2,4] oxadiazolyl, benzothiazolyl, where the carbocycles and the heterocycles can be mono- or polysubstituted by:

$-C_1 \ldots _6$-alkyl, $-O-C_1 \ldots _6$-alkyl, $-O-C_3 \ldots _7$-cycloalkyl, mono-, bi- or tricyclic saturated or mono- or polyunsaturated carbocycles having 3 . . . 14 ring members, mono-, bi- or tricyclic saturated or mono- or polyunsaturated heterocycles having 5 . . . 15 ring members and 1 . . . 6 heteroatoms, which are preferably N, O and S, $-F$, $-Cl$, $-Br$, $-I$, $-OH$, $-SH$, $-NO_2$, $-NH_2$, $-NHC_1 \ldots _6$-alkyl, $-N(C_1 \ldots _6$-alkyl$)_2$, $-NHC_6 \ldots _{14}$-aryl, $-N(C_6 \ldots _{14}$-aryl$)_2$, $-N(C_1 \ldots _6$-alkyl$)-(C_6 \ldots _{14}$-aryl), $-NHCOC_1 \ldots _6$-alkyl, $-NHCOC_6 \ldots _{14}$-aryl, $-CONHC_1 \ldots _6$-alkyl, $-CONHC_6 \ldots _{14}$-aryl, $-CONHSO_2C_1 \ldots _6$-alkyl, $-CONHSO_2C_6 \ldots _{14}$-aryl, $-CN$, $-(CO)C_1 \ldots _6$-alkyl, $-(CS)C_1 \ldots _6$-alkyl, $-COOH$, $-COOC_1 \ldots _6$-alkyl, $-O-C_6 \ldots _{14}$-aryl, $-O-(CO)C_1 \ldots _6$-alkyl, $-O-(CO)C_6 \ldots _{14}$-aryl, benzyl, benzyloxy, $-S-C_1 \ldots _6$-alkyl, $-S-C_6 \ldots _{14}$-aryl, $-CF_3$, $-(CH_2)_p-COOH$ where p=1 to 4, $-(CH_2)_p-COOC_1 \ldots _6$-alkyl where p=1 to 4, $-SO_2-C_1 \ldots _6$-alkyl, $-SO_2-C_6 \ldots _{14}$-aryl, $R^1$ can furthermore be H (but not if X=CH$_2$), $R^3-Z$ can furthermore be NO$_2$.

The compounds according to the invention are new, but excluding compounds as in formula I:

if Y=$-(CH_2)_p-(C=O)-$, $-(CH_2)_p-(C=O)-NH-$ where p=1 . . . 4, then $R^2$ must not be pyridine, piperazine, pyrimidine, tetrahydropyridine;

if z is $-NH-(C=O)-$, $-NH-(C=O)-NH-$, $-NH-(C=O)-O-$, $-NH-(C=O)-CH_2-$ and simultaneously $R^1$=phenyl, monosubstituted or polysubstituted by $-COOH$, $-COOC_1 \ldots _6$-alkyl, $-(CH_2)_p-COOH$, where p=1 to 4, $-(CH_2)_p-COOC_1 \ldots _6$-alkyl where p=1 . . . 4, $-CONHC_1 \ldots _6$-alkyl, $-CONHC_6 \ldots _{14}$-aryl, $-CONHSO_2C_1 \ldots _6$-alkyl, $-CONHSO_2C_6 \ldots _{14}$-aryl, 1H-tetra-zol-5-yl, then $R^2$ must not be phenyl, mono-substituted or polysubstituted by CN, halogen, $C_{1 \ldots 4}$-alkyl, $C_1 \ldots _4$-alkyloxy, CF$_3$;

if $R^3-Z=NO_2$, then $R^1-X$ and $R^2-Y$ must not simultaneously have the following meaning:

$R^1-X$=benzyl, 4-methoxybenzyl $R^2-Y$=benzyl, 2-picolyl.

The invention furthermore relates to the physiologically tolerable salts of the compounds according to formula I. The pharmacologically tolerable salts are obtained in a customary manner by neutralization of the bases with inorganic or organic acids or by neutralization of the acids with inorganic or organic bases. Possible inorganic acids are, for example, hydrochloric acid, sulphuric acid, phosphoric acid or hydrobromic acid, organic acids are, for example, carboxylic, sulpho or sulphonic acids such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, malic acid, salicylic acid, 3-aminosalicylic acid, ascorbic acid, embonic acid, nicotinic acid, isonicotinic acid, oxalic acid, amino acids, methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid. Possible inorganic bases are, for example, sodium hydroxide solution, potassium hydroxide solution, ammonia and organic bases are amines, preferably, however, tertiary amines, such as trimethylamine, triethylamine, pyridine, N,N-dimethylaniline, quinoline, isoquinoline, α-picoline, β-picoline, γ-picoline, quinaldine or pyrimidine.

In addition, physiologically tolerable salts of the compounds according to formula I can be obtained by converting derivatives which have tertiary amino groups into the corresponding quaternary ammonium salts in a manner known per se. Possible quaternizing agents are, for example, alkyl halides such as methyl iodide, ethyl bromide and n-propyl chloride, but also arylalkyl halides such as benzyl chloride or 2-phenylethyl bromide.

Furthermore, the invention of compounds of the formula I which contain an asymmetric carbon atom relates to the D form, the L form and D,L mixtures and, in the case of a number of asymmetric carbon atoms, the diastereomeric forms. Those compounds of the formula I which contain asymmetric carbon atoms and are obtained as a rule as racemates, can be separated into the optically active isomers in a manner known per se, for example using an optically active acid. However, it is also possible to employ an optically active starting substance from the beginning, a corresponding optically active or diastereomeric compound then being obtained as a final product.

The invention relates to the use of the compounds according to the invention or their physiologically tolerable salts as 1. inhibitors of PPIase for the production of medicaments for the treatment of diseases mediated by this enzyme and/or
2. inhibitors of late-phase eosinophilia for the production of medicaments for the treatment of diseases mediated by these cells.

These diseases include, for example, bronchial asthma, allergic rhinitis, allergic conjunctivitis, a topic dermatitis, eczema, allergic angiitis, inflammations mediated by eosinophils such as eosinophilic fasciitis, eosinophilic pneumonia and PIE syndrome, autoimmune diseases such as rheumatoid arthritis, rheumatoid spondylitis, lupus erythematosus, multiple sclerosis, psoriasis, glomerulonephritis and uveitis, insulin-dependent diabetes mellitus and sepsis. The compounds according to the invention or their physiologically tolerable salts are furthermore used for the production of medicaments for the prevention of rejection reactions after transplantation of cells, tissues or organs.

For the production of the medicaments, in addition to the customary auxiliaries, carriers and additives, an efficacious dose of the compounds according to the invention or their salts is used. The dose of the active compounds can vary depending on the administration route, age, weight of the patient, nature and severity of the diseases to be treated and similar factors. The daily dose can be given as an individual dose to be administered once or subdivided into two or more daily doses and is, as a rule, 0.001–1000 mg.

Possible administration forms are oral, parenteral, intravenous, transdermal, topical, inhalational and intranasal preparations.

For administration, possible customary pharmaceutical preparation forms are those such as tablets, coated tablets, capsules, dispersible powders, granules, aqueous solutions, aqueous or oily suspensions, syrup, juices or drops.

Solid pharmaceutical forms can contain inert ingredients and carriers, such as, for example, calcium carbonate, calcium phosphate, sodium phosphate, lactose, starch, mannitol, alginates, gelatin, guar gum, magnesium or aluminium stearate, methylcellulose, talc, highly disperse silicic acids, silicone oil, high molecular weight fatty acids (such as stearic acid), gelatin, agar-agar or vegetable or animal fats and oils, solid high molecular weight polymers (such as polyethylene glycol); preparations suitable for oral administration can contain, if desired, additional flavourings and/or sweeteners.

Liquid pharmaceutical forms can be sterilized and/or optionally contain auxiliaries such as preservatives, stabilizers, wetting agents, penetrating agents, emulsifiers, spreading agents, solubilizers, salts, sugars or sugar alcohols for regulating the osmotic pressure or for buffering, and/or viscosity regulators. Additives of this type are, for example, tartrate and citrate buffers, ethanol, complexing agents (such as ethylenediaminetetraacetic acid and its non-toxic salts). For regulating the viscosity, possible high molecular weight polymers are those such as, for example, liquid polyethylene oxide, microcrystalline celluloses, carboxymethylcelluloses, polyvinylpyrrolidones, dextrans or gelatin. Solid carriers are, for example, starch, lactose, mannitol, methylcellulose, talc, highly disperse silicic acids, high molecular weight fatty acids (such as stearic acid), gelatin, agar-agar, calcium phosphate, magnesium stearate, animal and vegetable fats, solid high molecular weight polymers such as polyethylene glycol.

Oily suspensions for parenteral or topical application can be vegetable synthetic or semi-synthetic oils such as, for example, liquid fatty acid esters in each case having 8 to 22 C atoms in the fatty acid chains, for example palmitic, lauric, tridecylic, margaric, stearic, arachic, myristic, behenic, pentadecanoic, linoleic, elaidic, brassidic, erucic or oleic acid, which are esterified with mono- to trihydric alcohols having 1 to 6 C atoms, such as, for example, methanol, ethanol, propanol, butanol, pentanol or their isomers, glycol or glycerol. Fatty acid esters of this type are, for example, commercially available Miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters such as artificial duck preen gland fat, isopropyl cocoate, oleyl oleate, decyl oleate, ethyl lactate, dibutyl phthalate, diisopropyl adipate, polyol fatty acid esters and others. Also suitable are silicone oils of differing viscosities or fatty alcohols such as isotridecyl alcohol, 2-octyldodecanol, cetylstearyl alcohol or oleyl alcohol, fatty acids such as, for example, oleic acid. It is furthermore possible to use vegetable oils such as castor oil, almond oil, olive oil, sesame oil, cottonseed oil, groundnut oil or soya bean oil.

Possible solvents, gelling agents and solubilizers are water or water-miscible solvents. Those suitable are, for example, alcohols such as, for example, ethanol or isopropyl alcohol, benzyl alcohol, 2-octyldodecanol, polyethylene glycols, phthalates, adipates, propylene glycol, glycerol, di- or tripropylene glycol, waxes, methylcellosolve, cellosolve, esters, morpholines, dioxane, dimethyl sulphoxide, dimethylformamide, tetrahydrofuran, cyclohexanone etc.

Film-forming agents which can be used are cellulose ethers which dissolve or swell both in water and in organic solvents, such as, for example, hydroxypropylmethylcellulose, methylcellulose, ethylcellulose or soluble starches.

Mixed forms between gel- and film-forming agents are also perfectly possible. Here, especially, ionic macromolecules are used, such as, for example, sodium carboxymethylcellulose, polyacrylic acid, polymethacrylic acid and its salts, sodium amylopectin semiglycolate, alginic acid or propylene glycol alginate as the sodium salt, gum arabic, xanthan gum, guar gum or carrageenan.

Further formulation auxiliaries which can be employed are: glycerol, paraffin of differing viscosities, triethanolamine, collagen, allantoin, novantisolic acid. The use of surfactants, emulsifiers or wetting agents can also be necessary for formulation, such as, for example, of Na laurylsulphate, fatty alcohol ether sulphates, di-Na N-lauryl-β-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenyl polyglycol ethers, cetyltrimethylammonium chloride or mono-/dialkyl polyglycol ether orthophosphoric acid monoethanolamine salts. Stabilizers such as montmorillonites or colloidal silicic acids for the stabilization of emulsions or for the prevention of the breakdown of the active substances, such as antioxidants, for example tocopherols or butylhydroxyanisole, or preservatives, such as p-hydroxybenzoic acid esters, can also be necessary for the preparation of the desired formulations.

The preparation, dispensation and sealing of the preparations is carried out under the customary antimicrobial and aseptic conditions.

The dose of the pharmaceutical preparations depends on the age, condition and weight of the patient and on the administration form. As a rule, the daily dose of active compound is between 0.001 and 25 mg/kg of body weight.

Preparation

According to the present invention, the compounds of the general formula I can be prepared by the following processes:

Process for the preparation of the compounds of the general formula I, according to claim 1, characterized in that a) for X=—$SO_2$—, —SO— the reaction is carried out according to scheme 1.

1H-Indazol-3-yl sulphonates II are reacted in the presence of a base and, if appropriate, in the presence of a diluent to give compounds of the general formula III, where $R^1_1$, $R^3$, X and Z have the abovementioned meaning. 1H-Indazol-3-yl sulphonates II or 1-sulphonylindazoles III are reacted, if appropriate in the presence of a base, in particular sodium hydride, and if appropriate in the presence of a diluent, in particular dimethyl sulphoxide, with compounds of the general formula Hal-Y-$R^2$ where $R^1$, $R^2$, $R^3$, X, Y and Z have the abovementioned meaning and Hal is a halogen atom F, Cl, Br or iodine, to give compounds of the general formula I, where $R^1$, $R^2$, $R^3$, X, Y and Z have the abovementioned meaning.

Scheme 1:

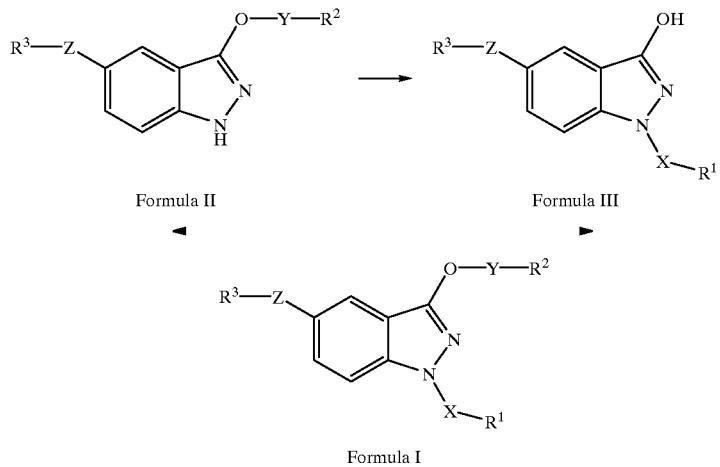

Formula II Formula III

Formula I b) for X=—$(CH_2)_p$—, —$(CH_2)_p$—O—, —$(CH_2)_p$—(C=O)—, —$(CH_2)_p$—(C=O)—NH—, —$(CH_2)_p$—CHOH—, —CHOH—$(CH_2)_p$—, —$(CH_2)_p$—CH=CH—, —CH=CH—$(CH_2)_p$— where p=1 . . . 4 the reaction is carried out according to scheme 2.

Compounds of the general formula III are reacted, if appropriate in the presence of a base, in particular sodium hydride, and if appropriate in the presence of a diluent, in particular dimethyl sulphoxide, with compounds of the general formula Hal-Y-$R^2$ where $R^1$, $R^2$, $R^3$, X, Y and Z have the abovementioned meaning and Hal is a halogen atom F, Cl, Br or iodine, to give compounds of the general formula I, where $R^1$, $R^2$, $R^3$, X, Y and Z have the abovementioned meaning.

Scheme 2:

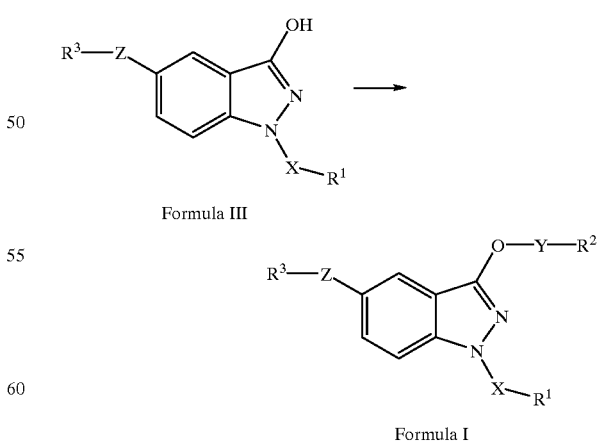

Formula III

Formula I where formula III can also be present as the tautomeric form formula IV according to scheme 3.

Scheme 3:

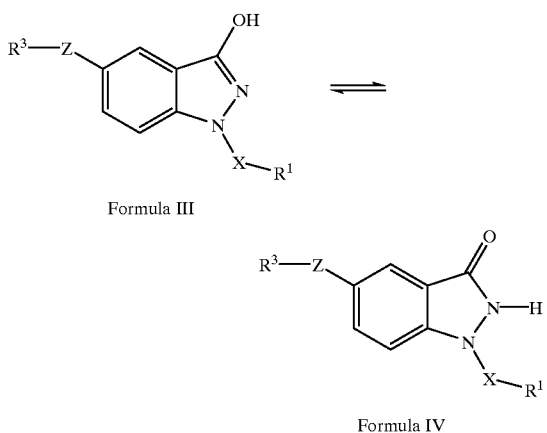

Formula III

Formula IV

The compounds of the general formula I are new.

WORKING EXAMPLES

The following representatives of the compounds according to the invention are mentioned by way of example:

3-[2-(2-bromo-4,6-difluorophenoxy)ethoxy]-5-methoxy-1-(toluene-4-sulphonyl)-1H-indazole 5-methoxy-1-(toluene-4-sulphonyl)-3-[5-(3-trifluoromethylphenyl)-1,2,4-oxadiazol-3-ylmethoxy]-1H-indazole 6-{2-[5-methoxy-1-(toluene-4-sulphonyl)-1H-indazol-3-yloxy]acetyl}-3,4-dihydro-1H-quinolin-2-one N-(2,4-difluorophenyl)-2-[5-methoxy-1-(toluene-4-sulphonyl)-1H-indazol-3-yloxy]acetamide 3-(6-chlorobenzo[1,3]dioxol-5-ylmethoxy)-5-methoxy-1-(3-nitrobenzyl)-1H-indazole 3-[3-(4-fluorophenyl)propoxy]-5-nitro-1-(3-nitrobenzyl)-1H-indazole 3-[3-(6-chlorobenzo[1,3]dioxol-5-ylmethoxy)-5-methoxyindazol-1-ylmethyl]phenylamine 1-(4-fluorobenzyl)-5-methoxy-3-[2-(4-nitrophenoxy)ethoxy]-1H-indazole 3-[2-(2-bromo-4,6-difluorophenoxy)ethoxy]-5-methoxy-1-[2-(4-nitrophenoxy)ethyl]-1H-indazole 3-[2-(2-bromo-4,6-difluorophenoxy)ethoxy]-1-[3,4-dichlorobenzyl]-5-methylthio-1H-indazole 1-{1-(2,4-dichlorobenzyl)-3-[2-(4-nitrophenoxy)ethoxy]-1H-indazol-5-yl}-3-naphthalen-1-ylurea The compounds are characterized by means of melting point, thin-layer chromatography, elemental analysis, NMR spectroscopy, IR and UV-VIS spectroscopy and optionally using mass spectroscopy.

Purification using column liquid chromatography: In the preparation of the compounds of Examples 1 to 123, the 1,2-dihydroindazol-3-ones according to the general formula V can be formed as by-products.

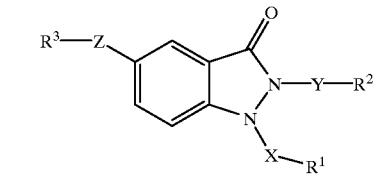

Formula V

The compounds of the general formula I can usually be separated from the compounds of the general formula V by recrystallization. If this is unsuccessful, a column-chromatographic separation under the following conditions is necessary: stationary phase: normal phase silica gel, e.g. Si 60 to 100 Å, particle size 5 to 100 μM. Eluent: methylene chloride/ethyl acetate=95/5 or methylene chloride/methanol=95/5. The compounds of the general formula V are more polar than the compounds of the general formula I, so the compounds of the general formula I are eluted first under these chromatographic conditions. This purification operation is applicable to all of Examples 1 to 123.

EXAMPLE 1

3-[2-(2-Bromo-4,6-difluorophenoxy)ethoxy]-5-methoxy-1-(toluene-4-sulphonyl)-1H-indazole

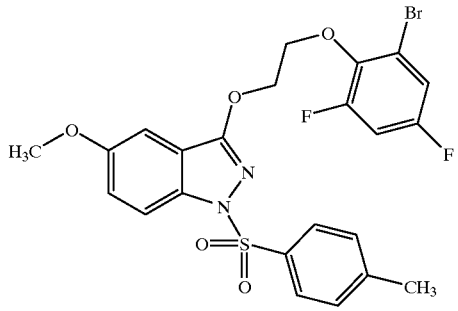

31.8 g (100 mmol) of 5-methoxy-1H-indazol-3-yl toluene-4-sulphonate are dissolved in 300 ml of DMSO and treated in portions with 3.54 g (140 mmol) of sodium hydride (95 per cent). After stirring for 15 minutes, a solution of 28.5 g (105 mmol) of 1-(2-bromo-4,6-difluorophenoxy)-2-chloroethane in 100 ml of DMSO is added dropwise and the mixture is stirred at 90° C. for 3 hours. After cooling, it is stirred into 1.5 l of water, the mixture is extracted three times with 400 ml of ethyl acetate each time, the organic phase is dried over sodium sulphate and distilled to dryness in vacuo, and the residue is recrystallized from ethanol.

Yield: 25.1 g (45.3% of theory); m.p. 133–134.5° C.; $^{13}$C-NMR (DMSO-$d_6$; 300 MHz): δ=21.3 $CH_3$; 55.9 $CH_3O$; 69.3 and 72.1 each $CH_2O$.

The starting materials used for the preparation of Examples 2 to 76 (Tables 1, 2, 3 and 4) were the following products:

5-methoxy-1H-indazol-3-yl toluene-4-sulphonate
5-methoxy-1H-indazol-3-yl 4-chlorobenzenesulphonate
5-methoxy-1H-indazol-3-yl 4-fluorobenzenesulphonate
5-methoxy-1H-indazol-3-yl 4-methoxybenzenesulphonate
5-methoxy-1H-indazol-3-yl 4-trifluoromethoxybenzenesulphonate
5-methoxy-1H-indazol-3-yl thiophene-2-sulphonate 5-methoxy-1H-indazol-3-yl 4-acetylaminobenzenesulphonate
5-methoxy-1H-indazol-3-yl quinoline-8-sulphonate
5-methoxy-1H-indazol-3-yl naphthalene-1-sulphonate
5-methoxy-1H-indazol-3-yl 2,5-dichlorobenzenesulphonate
4-(5-methoxy-1H-indazol-3-yloxysulphonyl)benzoic acid
5-nitro-1H-indazol-3-yl toluene-4-sulphonate
5-nitro-1H-indazol-3-yl 4-methoxybenzenesulphonate The synthesis of the compounds of Examples 2 to 31 is carried out analogously to the procedure according to Example 1. Further starting materials used are correspondingly $R^3$- and $(CH_2)_n$-substituted phenoxyalkyl bromides or chlorides.

TABLE 1

3-Phenoxyalkyloxyindazole-1-sulphonamides

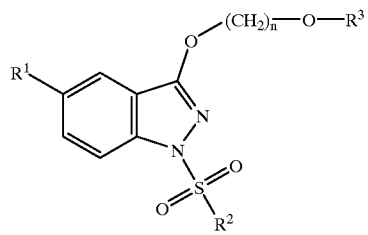

Formula VI $R^1 = CH_3O$

| Example | $R^2$ | $R^3$ | n | Yield (% of theory) | M.p. [° C.] | $^{13}$C-NMR (DMSO-$d_6$) $CH_2$ [ppm] |
|---|---|---|---|---|---|---|
| 2 | 4-Tolyl | Phenyl | 2 | 37 | 140 (2-PrOH) | 65.22; 68.26 |
| 3 | 4-Tolyl | Phenyl | 3 | 29 | 113–115 (2-PrOH) | 28.51; 64.24; 66.99 |
| 4 | 4-Tolyl | Phenyl | 4 | 22 | 136–137 (2-PrOH) | 25.37; 25.60 67.32; 69.75 |
| 5 | 4-Tolyl | 2-Bromo-phenyl | 2 | 6 | 123–125 (MeOH) | 64.92; 66.24 |
| 6 | 4-Tolyl | 4-Chloro-phenyl | 2 | 26 | 153 (2-PrOH) | 64.73; 67.13 |
| 7 | 4-Chloro-phenyl | 4-Chloro-phenyl | 2 | 9 | 149–154 (MeCN) | 66.24; 68.74 |
| 8 | 4-Fluoro-phenyl | 4-Chloro-phenyl | 2 | 29 | 121–126 (EtOH) | 65.48; 67.97 |
| 9 | 4-Methoxy-phenyl | 4-Chloro-phenyl | 2 | 37 | 160–162 (2-PrOH) | 66.26; 68.61 |
| 10 | 4-Tri-fluoro-methoxy-phenyl | 4-Chloro-phenyl | 2 | 22 | 117–120 (MeCN) | 66.24; 68.77 |
| 11 | 4-Tolyl | 2,6-Di-chloro-phenyl | 2 | 34 | 136–137.5 (MeCN) | 69.24; 71.42 |
| 12 | 4-Tolyl | 2,4-Di-fluoro-phenyl | 2 | 15 | 96–100 (EtOAc) | 67.87; 68.69 |
| 13 | 4-Tolyl | 2,6-Di-fluoro-phenyl | 2 | 21 | 101–102.5 (EtOH) | 69.35; 72.20 |
| 14 | 4-Tolyl | 2,4,6-Tri-fluoro-phenyl | 2 | 7 | 110–111.5 (EtOH) | 69.29; 72.45 |
| 15 | 4-Methoxy-phenyl | 2-Bromo-4,6-di-fluoro-phenyl | 2 | 10 | 119–121.5 (EtOAc) | 67.64; 70.49 |
| 16 | 4-Chloro-phenyl | 2-Bromo-4,6-di-fluoro-phenyl | 2 | 5 | 138–139.5 (EtOH) | 69.41; 72.05 |
| 17 | 4-Tolyl | 2,6-Di-bromo-4-nitro-phenyl | 2 | 16 | 131 (MeCN) | 69.17; 72.17 |

TABLE 1-continued

3-Phenoxyalkyloxyindazole-1-sulphonamides

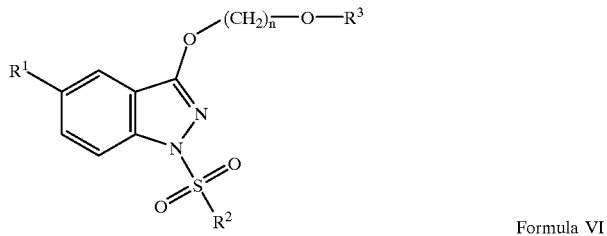

Formula VI

R¹ = CH₃O

| Example | R² | R³ | n | Yield (% of theory) | M.p. [° C.] | ¹³C-NMR (DMSO-d₆) CH₂ [ppm] |
|---|---|---|---|---|---|---|
| 18 | 4-Methoxyphenyl | 2,6-Dibromo-4-nitrophenyl | 2 | 14 | 153 (EtOH) | 69.72; 72.73 |
| 19 | 4-Tolyl | 4-Nitrophenyl | 2 | 9 | 152–156 (2-PrOH) | 66.92; 68.40 |
| 20 | 4-Chlorophenyl | 4-Nitrophenyl | 2 | 16 | 159–161 (MeCN) | 66.91; 68.49 |
| 21 | 4-Methoxyphenyl | 4-Nitrophenyl | 2 | 20 | 174–178 (2-PrOH) | 66.96; 68.37 |
| 22 | 2-Thiophenyl | 4-Nitrophenyl | 2 | 35 | 150–155 (MeOH) | 66.93; 69.58 |
| 23 | 4-Tolyl | 4-Cyanophenyl | 2 | 19 | 148–151 (2-PrOH) | 65.64; 67.65 |
| 24 | 4-Tolyl | 4-Carboxamidophenyl | 2 | 15 | 175–180 (2-PrOH) | 66.03; 68.62 |

Starting from 5-nitro-1H-indazol-3-yl toluene-4-sulphonate, the following derivatives were prepared analogously:

Formula VI, R¹ = NO₂

| Example | R² | R³ | n | Yield (% of theory) | M.p. [° C.] | ¹³C-NMR (DMSO-d₆) CH₂ [ppm] |
|---|---|---|---|---|---|---|
| 25 | 4-Tolyl | 4-Chlorophenyl | 2 | 58 | 150 (MeCN) | 65.05;68.10 |
| 26 | 4-Tolyl | 2,6-Dichlorophenyl | 2 | 35 | 117–125 (n-BuOH) | 69.88;71.21 |
| 27 | 4-Tolyl | 2,6-Difluorophenyl | 2 | 25 | 120 (n-BuOH) | 69.93;72.07 |
| 28 | 4-Tolyl | 2,6-Dibromo-4-nitrophenyl | 2 | 48 | 159 (n-BuOH) | 69.88;72.14 |
| 29 | 4-Tolyl | 4-Nitrophenyl | 2 | 20 | 212–216 (MeCN) | 65.39;67.54 |

By reduction of the 5-nitro group corresponding to the procedure as in to Example 87, the following derivatives were prepared:

Formula VI, R¹ = NH₂

| Example | R² | R³ | n | Yield (% of theory) | M.p. [° C.] | ¹³C-NMR (DMSO-d₆) CH₂ [ppm] |
|---|---|---|---|---|---|---|
| 30 | 4-Tolyl | 4-Chlorophenyl | 2 | 86 | 192.5–195 (2-PrOH) | 66.31;68.20 |
| 31 | 4-Tolyl | 2,6-Dibromo-4-nitrophenyl | 2 | 73 | 169 (2-PrOH) | 68.68;71.30 |

EXAMPLE 32

5-Methoxy-1-(toluene-4-sulphonyl)-3-[5-(3-trifluoromethylphenyl)-1,2,4-oxadiazol-3-ylmethoxy]-1H-indazole

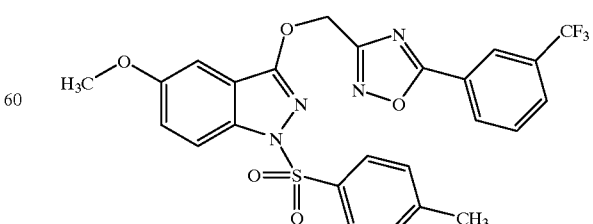

3.06 g (9.5 mmol) of 5-methoxy-1H-indazol-3-yl toluene-4-sulphonate are dissolved in 50 ml of DMSO and treated in portions with 0.34 g (14.2 mmol) of sodium hydride (95 per cent). After stirring for 15 minutes, a solution of 2.5 g (9.5 mmol) of 3-chloromethyl-5-[3-(trifluoromethyl)phenyl]-1,2,4-oxadiazole in 20 ml of DMSO are added dropwise and the mixture is stirred at 60° C. for 3 hours. After cooling, it is stirred into 200 ml of water, stirred for 6 hours, and the precipitate is filtered off with suction and recrystallized from ethanol.

Yield: 1.9 g (36.7% of theory); m.p. 138–144° C.; $^{13}$C-M (DMSO-d$_6$; 300 MHz): δ=19.0 CH$_3$; 54.1 CH$_3$O; 60.0 CH$_2$O.

The synthesis of the compounds of Examples 33 to 50 is carried out analogously to the procedure as in Example 32.

TABLE 2

3-Benzyloxyindazole-1-sulphonamides or heteroanalogues

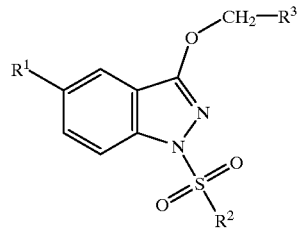

Formula VII $R^1 = CH_3O$

| Example | R$^2$ | R$^3$ | Yield (% of theory) | M.p. [° C.] | $^{13}$C-NMR (DMSO-d$_6$) CH$_2$ [ppm] |
|---|---|---|---|---|---|
| 33 | 4-Tolyl | 4-Benzyl-oxyphenyl | 23 | 159–161 (MeCN) | 70.51; 71.52 |
| 34 | 4-Tolyl | 2-Methoxy-5-acetylphenyl | 15 | 132–136 (EtOH) | 65.67 |
| 35 | 4-Tolyl | 2-Fluoro-6-chlorophenyl | 21 | 156–160 (2-PrOH) | 61.76 |
| 36 | 4-Chloro-phenyl | 2-Fluoro-6-chlorophenyl | 23 | 151–155 (EtOH) | 62.78 |
| 37 | 4-Fluoro-phenyl | 3-Trifluoro-methylphenyl | 10 | 113 (MeOH) | 70.48 |
| 38 | 4-Tolyl | 2-Fluoro-phenyl | 23 | 151–152 (2-PrOH) | 65.43 |
| 39 | 4-Fluoro-phenyl | 2-Fluoro-phenyl | 18 | 149–150 (MeCN) | 66.39 |
| 40 | 4-Fluoro-phenyl | 4-Fluoro-phenyl | 9 | 110–114 (EtOH) | 69.16 |
| 41 | 4-Tolyl | 4-Chloro-2-nitrophenyl | 25 | 85–90 (2-PrOH) | 67–74 |
| 42 | 4-Tolyl | 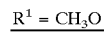 | 34 | 198–202 (MeCN) | 68.68; 102.66 |
| 43 | 4-Tolyl | 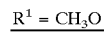 | 19 | 183–184 (EtOAc) | 65.35; 65.63; 91.49 |
| 44 | 4-Tolyl | 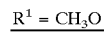 | 10 | 248–252 (MeCN) | 65.25; 65.79; 92.38 |

TABLE 2-continued

3-Benzyloxyindazole-1-sulphonamides or heteroanalogues

Formula VII

R¹ = CH₃O

| Example | R² | R³ | Yield (% of theory) | M.p. [° C.] | ¹³C-NMR (DMSO-d₆) CH₂ [ppm] |
|---|---|---|---|---|---|
| 45 | 4-Fluoro-phenyl | 6-nitro-4H-1,3-benzodioxine (Z at 8-position) | 10 | 246–250 (MeCN) | 64.55; 65.93; 91.58 |
| 46 | 4-Tolyl | 3,5-dimethylisoxazol-4-yl (Z) | 10 | 168–174 (EtOH) | 62.82 |
| 47 | 4-Chloro-phenyl | 3,5-dimethylisoxazol-4-yl (Z) | 14 | 180–182 (EtOH) | 60.92 |
| 48 | 4-Tolyl | 5-(2-methoxyphenyl)-1,2,4-oxadiazol-3-yl (Z) | 41 | 153–157 (MeCN) | 61.27 |
| 49 | 4-Tolyl | 5-(4-tert-butylphenyl)-1,2,4-oxadiazol-3-yl (Z) | 5 | 172–174 (EtOH) | 61.34 |
| 50 | 4-Tolyl | 2-(4-chlorophenyl)thiazol-4-yl (Z) | 23 | 180–181 (MeCN) | 67.77 |

EXAMPLE 51

6-{2-[5-Methoxy-1-(toluene-4-sulphonyl)-1H-indazol-3-yloxy]acetyl}-3,4-dihydro-1H-quinolin-2-one

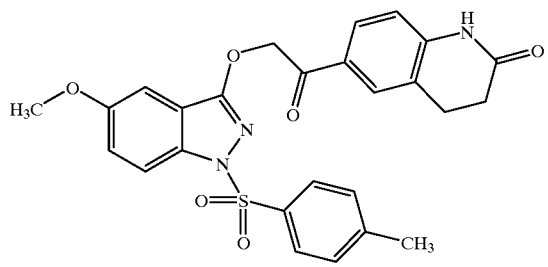

3.66 g (11.5 mmol) of 5-methoxy-1H-indazol-3-yl toluene-4-sulphonate are dissolved in 50 ml of DMSO and treated in portions with 0.41 g (17.2 mmol) of sodium hydride (95 per cent). After stirring for 15 minutes, a solution of 3.16 g (11.5 mmol) of 6-bromoacetyl-2-oxo-1,2,3,4-tetrahydroquinoline in 30 ml of DMSO is added dropwise and the mixture is stirred at 60° C. for 3 hours. After cooling, it is stirred into 200 ml of water, stirred for 6 hours, and the precipitate is filtered off with suction and recrystallized from acetonitrile.

Yield: 2.2 g (37.8% of theory); M.p. 232–237° C.; $^{13}$CNMR (DMSO-$d_6$; 300 MHz); δ=21.4 $CH_3$; 23.2 $CH_2$; 28.7 $CH_2$; 56.1 $CH_3O$; 69.5 $CH_2O$; 189.3 2 x C=O. IR (KBr): 1680 C=O.

The synthesis of the compounds of Examples 52 to 65 is carried out analogously to the procedure as in Example 51.

TABLE 3

3-Phenacylindazole-1-sulphonamide

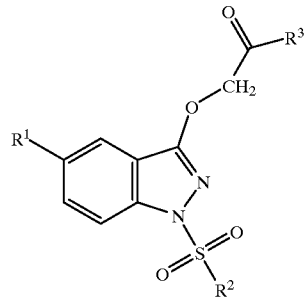

Formula VIII $R^1 = CH_3O$

| Example | $R^2$ | $R^3$ | Yield (% of theory) | M.p. [° C.] | $^{13}$C-NMR (DMSO-$d_6$) $CH_2O/C=O$ |
|---|---|---|---|---|---|
| 52 | 4-Tolyl | 4-Chloro-phenyl | 7 | 173–180 (MeCN) | 70.00/190.55 |
| 53 | 4-Methoxy-phenyl | 4-Chloro-phenyl | 37 | 183–183.5 (MeCN) | 70.59/191.38 |
| 54 | 4-Chloro-phenyl | 4-Chloro-phenyl | 21 | 166–169 (2-PrOH) | 72.50/192.84 |
| 55 | 4-Tolyl | 3,4-Di-chloro-phenyl | 9 | 173–178 (MeCN) | 72.65/192.52 |
| 56 | 4-Chloro-phenyl | 3,4-Di-chloro-phenyl | 13 | 175–178 (MeCN) | 70.42/190.03 |
| 57 | 4-Acetyl-amino-phenyl | 3,4-Di-chloro-phenyl | 4 | 225–229 (EtOH) | 71.51/191.47 |
| 58 | Naphthalen-1-yl | 3,4-Di-chloro-phenyl | 17 | 210–212 (MeCN) | 70.97/190.68 |
| 59 | Quinolin-8-yl | 3,4-Di-chloro-phenyl | 33 | 213–218 (MeCN) | 71.19/191.43 |
| 60 | 4-Tolyl | 4-Diphenyl | 8 | 196–200 (MeCN) | 73.54/194.35 |
| 61 | 4-Chloro-phenyl | 4-Diphenyl | 44 | 207–210 (MeCN) | 73.04/193.65 |
| 62 | 4-Methoxy-phenyl | 4-Diphenyl | 23 | 198–205 (MeCN) | 71.55/192.43 |
| 63 | 4-Acetyl-amino-phenyl | 4-Diphenyl | 2 | 248–249 (n-BuOH) | 71.53/192.47 |

Starting from 5-nitro-1H-indazol-3-yl toluene-4-sulphonate, the following derivatives were prepared analogously:

| | | | Formula VIII, $R^1$ = $NO_2$ | | |
|---|---|---|---|---|---|
| Example | $R^2$ | $R^3$ | Yield (% of theory) | M.p. [° C.] | $^{13}$C-NMR (DMSO-$d_6$) $CH_2O/C=O$ |
| 64 | 4-Tolyl | 4-Chlorophenyl | 35 | 201–207 (MeOH) | 72.06/191.74 |

By reduction of the 5-nitro group corresponding to the procedure as in Example 87, the following derivatives were prepared:

| | | | Formula VIII, $R^1$ = $NH_2$ | | |
|---|---|---|---|---|---|
| Example | $R^2$ | $R^3$ | Yield (% of theory) | M.p. [° C.] | $^{13}$C-NMR (DMSO-$d_6$) $CH_2O/C=O$ |
| 65 | 4-Tolyl | 4-Chlorophenyl | 64 | 193–195.5 (2-PrOH) | 71.28/192.18 |

EXAMPLE 66
N-(2,4-Difluorophenyl)-2-[5-methoxy-1-(toluene-4-sulphonyl)-1H-indazol-3-yloxy]acetamide

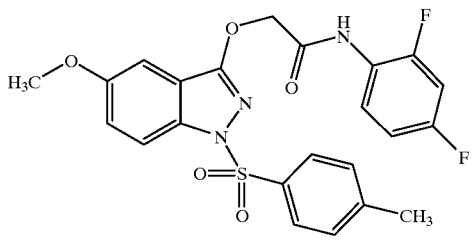

3.66 g (11.5 mmol) of 5-methoxy-1H-indazol-3-yl toluene-4-sulphonate are dissolved in 50 ml of DMSO and treated in portions with 0.41 g (17.2 mmol) of sodium hydride (95 per cent). After stirring for 15 minutes, a solution of 2.36 g (11.5 mmol) of α-chloro-2,4-difluoroacetanilide in 20 ml of DMSO is added dropwise and the mixture is stirred at 60° C. for 3 hours. After cooling, it is stirred into 200 ml of water, stirred for 6 hours, and the precipitate is filtered off with suction and recrystallized from methanol. The recrystallized precipitate is filtered off with suction (by-product), the filtrate is concentrated to 30 ml and, after crystallization is complete, the product is filtered off with suction.

Yield: 1.0 g (17.8% of theory); m.p. 155–159° C.; $^{13}$C-NMR (DMSO-$d_6$; 300 MHz): δ=20.8 $CH_3$; 55.7 $CH_3O$; 67.2 $CH_2O$; 165.4 C=O. IR (KBr): 1706 C=O.

The synthesis of the compounds of Examples 67 to 76 is carried out analogously to the procedure as in Example 66.

TABLE 4

Other 3-subst. indazol-1-sulphonamides

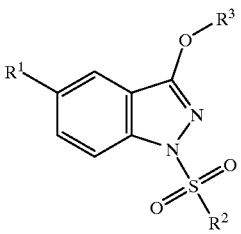

Formula IX $R^1$ = $CH_3O$

| Example | $R^2$ | $R^3$ | Yield (% of theory) | M.p. [° C.] | $^{13}$C-NMR (DMSO-$d_6$) $CH_2O$ [ppm] |
|---|---|---|---|---|---|
| 67 | 4-Tolyl | 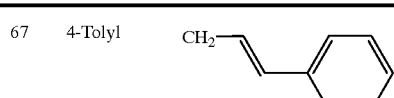 | 16 | 128–129 (2-PrOH) | 70.13 |
| 68 | 4-Tolyl | 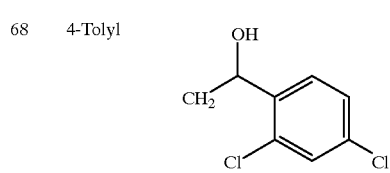 | 5 | 135–140 (EtOH) | 72.79 |

TABLE 4-continued

Other 3-subst. indazol-1-sulphonamides

Formula IX $R^1 = CH_3O$

| Example | $R^2$ | $R^3$ | Yield (% of theory) | M.p. [° C.] | $^{13}$C-NMR (DMSO-$d_6$) CH$_2$O [ppm] |
|---|---|---|---|---|---|
| 69 | 4-Tolyl | -CH$_2$-C(O)-C$_6$H$_4$-OCH$_3$ | 18 | 142–144 (EtOH) | 67.08 |
| 70 | 4-Fluoro-phenyl | -CH$_2$-C(O)-C$_6$H$_4$-OCH$_3$ | 6 | 154–157 (MeCN) | 69.58 |
| 71 | 4-Tolyl | -CH$_2$-C(O)-C$_6$H$_4$-F | 5 | 165–169 (MeOH) | 69.40 |
| 72 | 4-Tolyl | -CH$_2$-C(O)-NH-C$_6$H$_4$-OCH$_3$ | 29 | 177–178.5 (EtOH) | 67.97 |
| 73 | 4-Tolyl | -CH$_2$-C(O)-NH-C$_6$H$_3$-Cl$_2$ | 39 | 196–200 (MeCN) | 67.79 |
| 74 | 4-Tolyl | -CH$_2$-C(O)-NH-CH$_2$-C$_6$H$_5$ | 24 | 147–151 (EtOH) | 65.86 |
| 75 | 4-Tolyl | -CH$_2$-(3-quinazoline-2,4-dione) | 14 | 238–241 (MeCN) | 67.20 |

TABLE 4-continued

Other 3-subst. indazol-1-sulphonamides

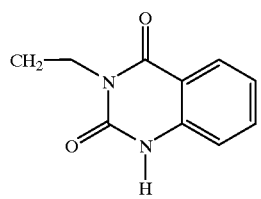

Formula IX $R^1 = CH_3O$

| Example | $R^2$ | $R^3$ | Yield (% of theory) | M.p. [° C.] | $^{13}$C-NMR (DMSO-$d_6$) $CH_2O$ [ppm] |
|---|---|---|---|---|---|
| 76 | 4-Methoxy-phenyl | (structure) | 24 | 216 dec. (MeCN) | 66.85 |

EXAMPLE 77

3-(6-Chlorobenzo[1,3]dioxol-5-ylmethoxy)-5-methoxy-1(3-nitrobenzyl)-1H-indazole

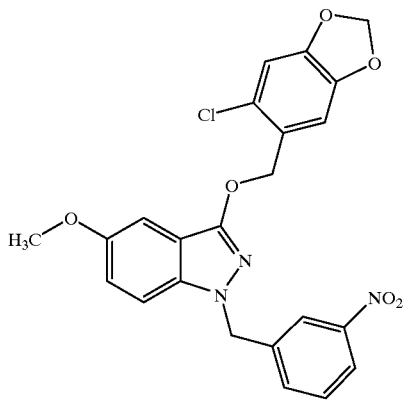

4.5 g (15 mmol) of 5-methoxy-1-(3-nitrobenzyl)-1H-indazol-3-ol are dissolved in 100 ml of DMSO and treated in portions with 0.72 g (18 mrnol) of sodium hydride (60 per cent). After stirring for 2 hours, a solution of 3.1 g (15 mmol) of 6-chloropiperonyl chloride in 20 ml of DMSO is added dropwise and the mixture is stirred at 60° C. for 3 hours. After cooling, 250 ml of water are added dropwise, the mixture is stirred for 4 hours and the solid is filtered off with suction. The precipitate is first recrystallized from isopropanol, then from ethanol.

Yield: 3.3 g (47.0% of theory); m.p. 134–135.5° C.; $^{13}$C-NMR (DMSO-$d_6$; 300 MHz): δ=51.5 $CH_2N$; 55.7 $CH_3O$; 67.8 $CH_2O$; 101.7 $OCH_2O$.

The synthesis of the compounds of Examples 78 to 85 is carried out analogously to the procedure as in Example 77.

TABLE 5

1-(3-Nitrobenzyl)-3-alkyloxyindazoles

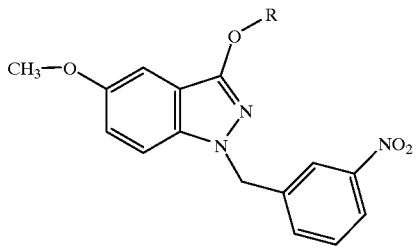

Formula XI

| Example | R | Yield (% of theory) | M.p. [° C.] | $^{13}$C-NMR (DMSO-$d_6$) N—CH$_2$/O—CH$_2$ |
|---|---|---|---|---|
| 78 | 4-Chlorophenoxyethyl | 31 | 118–120 (2-PrOH) | 51.46/66.68; 67.32 |
| 79 | 4-Nitrophenoxyethyl | 75 | 163–166 (acetone) | 50.48/67.03; 67.10 |
| 80 | 4-Carboxaminophenoxy-ethyl | 94 | 159–162 (EtOH) | 50.47/66.22; 67.28 |
| 81 | 2-Bromo-4,6-difluorophenoxyethyl | 44 | 63–73 (2-PrOH) | 52.01/68.32; 72.80 |
| 82 | 2,6-Dibromo-4-nitrophenoxyethyl | 18 | 118–121 (EtOAc) | 51.95/68.09; 72.59 |
| 83 | CH$_2$-(4-pyridyl) H—Cl | 55 | 160–170 (acetone) | 50.39/68.30 |
| 84 | 2,6-Dichlorobenzyl | 61 | 139–143 (EtOH) | 50.49/65.31 |
| 85 | CH$_2$—C(O)—C$_6$H$_4$—Cl | 53 | 141–144 (2-PrOH) | 51.91/71.00 |

EXAMPLE 86

3-[3-(4-Fluorophenyl)propoxy]-5-nitro-1-(3-nitrobenzyl)-1H-indazole

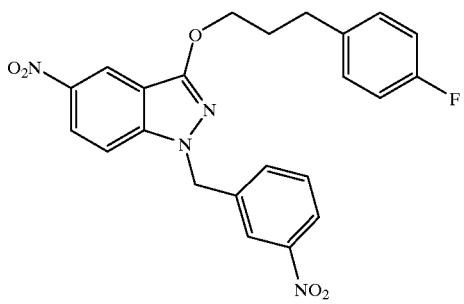

5.97 g (19 mmol) of 5-nitro-1-(3-nitrobenzyl)-1H-indazol-3-ol and 4.47 g (29 mmol) of 3-(4-fluorophenyl)propan-1-ol are dissolved in 150 ml of tetrahydrofuran and treated with 7.6 g (29 mmol) of triphenylphosphine. A solution of 5.1 g (29 mmol) of diethyl azodicarboxylate in 10 ml of tetrahydrofuran is then added dropwise and the mixture is stirred at 20 to 25° C. for 5 hours. It is then distilled to dryness in vacuo, the residue is stirred with 50 ml of 1N sodium hydroxide solution for 2 hours and neutralized with 5 ml of 10N hydrochloric acid, and the aqueous supernatant is decanted. The oily product is crystallized by stirring with methanol and recrystallized from n-butanol.

Yield: 4.7 g (54.9% of theory); m.p. 85–90° C.; $^{13}$C-NMR (DMSO-$d_6$; 300 MHz); δ=30.35 CH$_2$; 30.91 CH$_2$; 51.15 CH$_2$N; 68.95 CH$_2$O.

EXAMPLE 87

3-[3-(6-Chlorobenzo[1,3]dioxol-5-ylmethoxy)-5-methoxyindazol-1-ylmethyl]phenylamine

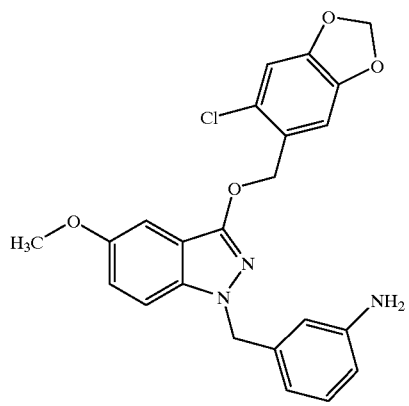

2.2 g (4.7 mmol) of 3-(6-chlorobenzo[1,3]dioxol-5-yl-methoxy)-5-methoxy-1-(3-nitrobenzyl)-1H-indazole are dissolved in 500 ml of dioxane, treated with about 1 g of Raney nickel and hydrogenated for 2 hours at 70° C., 20 bar. After cooling, the catalyst is filtered off with suction, the filtrate is distilled to dryness in vacuo and the residue is recrystallized from dioxane.

Yield: 1.8 g (87.5% of theory); m.p. 153–154° C.; $^{13}$C-NMR (DMSO-$d_6$; 300 MHz): δ=52.6 $CH_2N$; 55.7 $CH_3O$; 67.9 $CH_2O$; 101.7 $OCH_2O$.

The synthesis of the compounds of Examples 88 to 90 is carried out analogously to the procedure as in Example 87.

TABLE 6

1-(3-Aminobenzyl)-3-alkyloxyindazoles

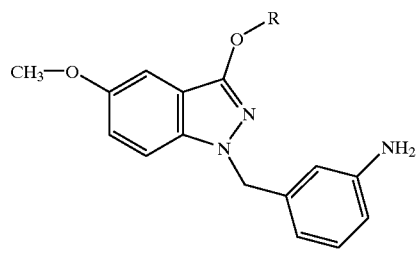

Formula XII

| Example | R | Yield (% of theory) | M.p. [° C.] | $^{13}$C-NMR (DMSO-$d_6$) N—$CH_2$/O—$CH_2$ |
|---|---|---|---|---|
| 88 | CH₂—O—C₆H₄—NH₂  2 H—Cl | 89 | 227–230 (2-PrOH) | 50.99/66.63; 67.35 |
| 89 | CH₂—O—C₆H₄—C(O)NH₂ | 77 | 176–178 (dioxane) | 52.00/66.43; 67.33 |
| 90 | CH₂—C(O)—C₆H₄—Cl  H—Cl | 40 | 155–158 (2-PrOH) | 50.84/70.57 |

EXAMPLE 91

1-(4-Fluorobenzyl)-5-methoxy-3-[2-(4-nitrophenoxy)ethoxy]-1H-indazole

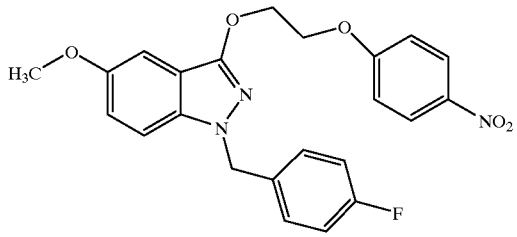

4.1 g (15 mmol) of 1-(4-fluorobenzyl)-5-methoxy-1H-indazol-3-ol are dissolved in 100 ml of DMSO and treated in portions with 1 g (25 mmol) of sodium hydride (60 per cent). After stirring for 2 hours, a solution of 3.7 g (15 mmol) of 2-(4-nitrophenoxy)ethyl bromide in 20 ml of DMSO is added dropwise and the mixture is stirred at 80–90° C. for 3 hours. After cooling, 250 ml of water are added dropwise, the mixture is stirred for 4 hours, and the solid is filtered off with suction and recrystallized from ethanol.

Yield: 3.1 g (47.2% of theory); m.p. 117–120.5° C.; $^{13}$C-NMR (DMSQ-$d_6$; 300 MHz): δ=50.7 $CH_2N$; 55.4 $CH_3O$; 67.0 $CH_2O$; 67.2 $CH_2O$.

The synthesis of the compounds of Examples 92 to 98 is carried out analogously to the procedure as in Example 91.

TABLE 7

1-(4-Fluorobenzyl)-3-alkoxyindazoles

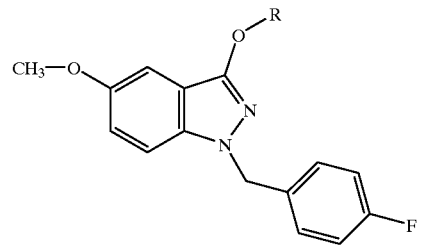

Formula XIII

| Example | R | Yield (% of theory) | M.p. [° C.] | $^{13}$C-NMR (DMSO-$d_6$) N—$CH_2$/O—$CH_2$ |
|---|---|---|---|---|
| 92 | CH₂—O—C₆H₄—Cl | 48 | 81.5–83.5 (EtOH) | 50.51/65.49; 65.99 |
| 93 | CH₂—O—C₆H₄—NH₂ · 2 HCl | 75 | 190–195 (2-PrOH) | 50.73/66.52; 67.21 |
| 94 | CH₂—O—C₆H₂(F)(F)(Br) | 40 | 64–66 (2-PrOH) | 52.22/68.27; 72.93 |
| 95 | CH₂-(3,5-dimethylisoxazol-4-yl) | 84 | 97–98 (EtOH) | 52.25/60.10 |
| 96 | CH₂—C₆H₂(F)(F)(F) | 73 | 72–75 (EtOH) | 51.96/58.57 |

TABLE 7-continued 1-(4-Fluorobenzyl)-3-alkoxyindazoles

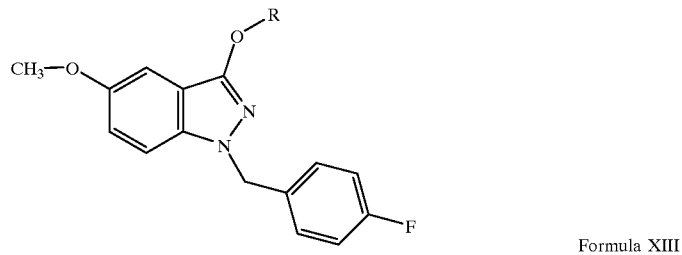

Formula XIII

| Example | R | Yield (% of theory) | M.p. [° C.] | $^{13}$C-NMR (DMSO-$d_6$) N—CH$_2$/O—CH$_2$ |
|---|---|---|---|---|
| 97 | CH$_2$-[5-chloro-1,3-benzodioxol-6-yl] | 75 | 135–136.5 (2-PrOH) | 52.31/68.32 |
| 98 | CH$_2$-C(=O)-(4-chlorophenyl)  H—Cl | 73 | 119–121 (EtOH) | 53.79/72.73 |

EXAMPLE 99

3-[2-(2-Bromo-4,6-difluorophenoxy)ethoxy]-5-methoxy-1-[2-(4-nitrophenoxy)ethyl]-1H-indazole

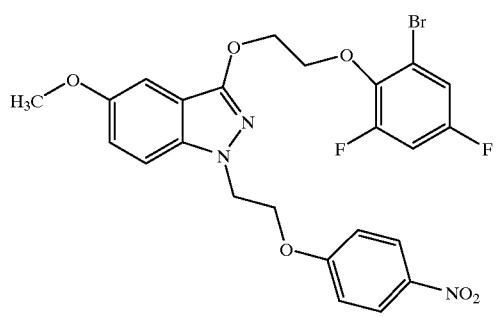

2.7 g (8 mmol) of 5-methoxy-1-[2-(4-nitrophenoxy)ethyl]-1H-indazol-3-ol are dissolved in 50 ml of DMSO and treated in portions with 0. 4 g (16.7 mmnol) of sodium hydride (95 per cent). After stirring for 15 minutes, a solution of 2.17 g (8 mmol) of 1-(2-bromo-4,6-difluorophenoxy)-2-chloroethane in 20 ml of DMSO is added dropwise and the mixture is stirred at 60° C. for 3 hours. After cooling, 200 ml of water are added, the mixture is stirred for 6 hours, and the solid is filtered off with suction and recrystallized from ethanol.

Yield: 1.7 g (37.6% of theory); m.p. 102° C.; $^{13}$C-NMR (DMSQ-$d_6$; 300 MHz): δ=46.3 CH$_2$N; 54.3 CH$_3$O; 66.6 CH$_2$O; 66.9 0H$_2$O; 71.3 CH$_2$O.

The synthesis of the compounds of Examples 100 to 111 is carried out analogously to the procedure as in Example 99.

TABLE 8
1-(Phenoxyethyl)-3-alkyloxyindazoles
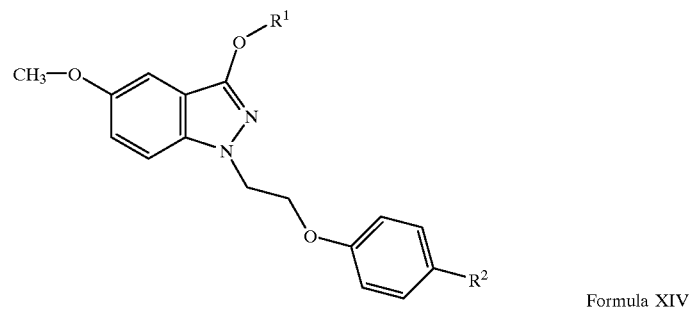
Formula XIV
$R^2 = NO_2$
| Example | R[1] | Yield (% of theory) | M.p. [° C.] | $^{13}$C-NMR (DMSO-$d_6$) OCH$_2$ |
|---|---|---|---|---|
| 100 | CH$_2$—O—C$_6$H$_4$—Cl | 48 | 110–116 (EtOH) | 67.86; 68.55; 68.84 |
| 101 | CH$_2$—O—(2,6-Br$_2$-4-NO$_2$-C$_6$H$_2$) | 18 | 157–161 (EtOAc) | 65.90; 66.06; 70.53 |
| 102 | CH$_2$—C(O)—C$_6$H$_4$—Cl | 33 | 181–184 (MeCN) | 68.21; 71.36 |
| 103 | CH$_2$—C(O)—(3,4-Cl$_2$-C$_6$H$_3$) | 29 | 195–197 (MeCN) | 66.91; 70.44 |
| 104 | CH$_2$—C(O)—(4-phenyl-C$_6$H$_4$) | 63 | 153–156 (MeCN) | 67.71; 70.89 |
| 105 | CH$_2$—C(O)—(6-(2-oxo-1,2,3,4-tetrahydroquinolinyl)) | 50 | 158–165 (MeCN) | 67.78; 70.60 |
| 106 | CH$_2$—C(O)—NH—(2,4-F$_2$-C$_6$H$_3$) | 40 | 167–171 (MeCN) | 67.51; 67.03 |

TABLE 8-continued
1-(Phenoxyethyl)-3-alkyloxyindazoles
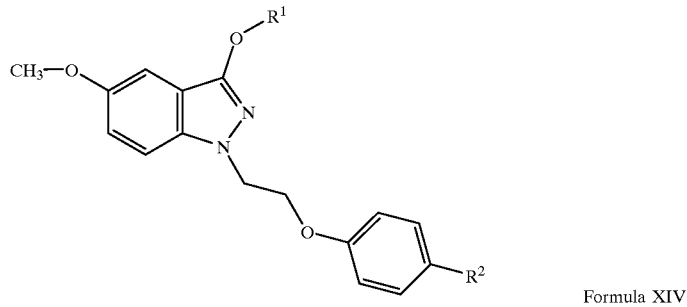
Formula XIV
R² = NO₂
| Example | R¹ | Yield (% of theory) | M.p. [° C.] | ¹³C-NMR (DMSO-d₆) OCH₂ |
|---|---|---|---|---|
| 107 | 3-CH₂-, 4-methoxy-acetophenone group | 55 | 91–98 (EtOH) | 64.69; 66.97 |
| 108 | 3-(trifluoromethyl)benzyl | 47 | 91–96 (EtOH) | 67.87; 69.65 |
| 109 | 2-fluorobenzyl | 60 | 144–147 (MeCN) | 64.50; 67.89 |
| 110 | 6-fluoro-4H-1,3-benzodioxin-8-ylmethyl | 53 | 177–178.5 (MeCN) | 63.93; 64.82; 67.04; 90.63 |

| | Formula XIV | | | |
|---|---|---|---|---|
| | $R^2$ = Cl | | | |
| Example | $R^1$ | Yield (% of theory) | M.p. [° C.] | $^{13}$C-NMR (DMSO-$d_6$) OCH$_2$ |
| 111 | CH$_2$—O—C$_6$H$_4$—Cl | 6 | 110–116 (EtOH) | 66.92; 67.32; 67.60 |

EXAMPLE 112

3-[2-(2-Bromo-4,6-difluorophenoxy)ethoxy]-1-[3,4-dichlorobenzyl]-5-methylthio-1H-indazole

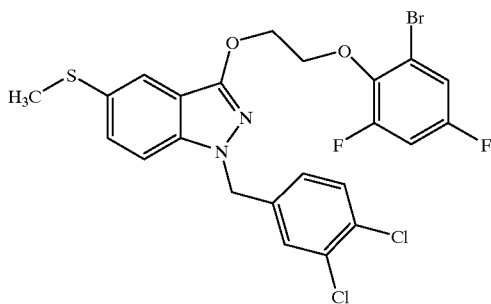

3.6 g (11 mmol) of 1-(3,4-dichlorobenzyl)-5-methylthio-1H-indazol-3-ol are dissolved in 100 ml of DMSO and treated in portions with 0.34 g (13.2 mmol) of sodium hydride (95 per cent). After stirring for 2 hours, a solution of 3.0 g (11 mmol) of 1-(2-bromo-4,6-difluorophenoxy)-2-chloroethane in 20 ml of DMSO is added dropwise and the mixture is stirred at 60° C. for 3 hours. After cooling, 200 ml of water are added dropwise, the mixture is extracted three times with 100 ml of ethyl acetate each time, and the combined organic phases are washed with 50 ml of water, dried over sodium sulphate and distilled to dryness in vacuo. The residue is dissolved in 100 ml of chloroform, extracted by shaking with 100 ml each of 1N sodium hydroxide solution and 100 ml of water, the organic phase is dried over sodium sulphate and distilled to dryness, and the residue is purified by means of liquid chromatography (silica gel 60/0.2–0.5 mm, eluent methylene chloride/methanol=9/1).

Yield: 0.3 g (5% of theory); m.p. 46–49° C.; $^{13}$C-NMR (DMSO-$d_6$; 300 MHz); δ=18.4 CH$_3$S; 51.7 CH$_2$N; 68.3 CH$_2$O; 72.7 CH$_2$O.

The synthesis of the compound of Example 113 is carried out analogously to the procedure as in Example 112.

TABLE 9

Subst. 1-benzyl-3-alkyloxy-5-methylthioindazoles

Formula XIV

| Example | R | Yield (% of theory) | M.p. [° C.] | $^{13}$C-NMR (DMSO-$d_6$) N—CH$_2$/O—CH$_2$ |
|---|---|---|---|---|
| 113 | CH$_2$—C(=O)—C$_6$H$_4$—Cl | 74 | 134–139 (EtOH) | 51.62/71.09 |

EXAMPLE 114

1-{1-(2,4-Dichlorobenzyl)-3-[2-(4-nitrophenoxy)ethoxy]-1H-indazol-5-yl}-3-naphthalen-1-ylurea

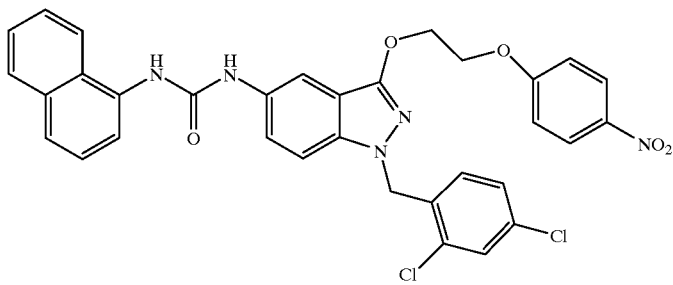

2.9 g (6.1 mmol) of 1-[1-(2,4-dichlorobenzyl)-3-hydroxy-1H-indazol-5-yl]-3-naphthalen-1-ylurea are dissolved in 70 ml of DMSO and treated in portions with 0.22 g (9 mmol) of sodium hydride (95 per cent). After stirring for 10 minutes, a solution of 1.5 g (6.1 mmol) of 2-(4-nitrophenoxy)ethyl bromide in 10 ml of DMSO is added dropwise and the mixture is stirred at 60° C. for 3 hours. After cooling, 400 ml of water are added, and the mixture is stirred for 3 hours and extracted three times with 400 ml of ethyl acetate. The combined organic phases are washed with 100 ml of water, dried over sodium sulphate, distilled to dryness in vacuo and the residue is recrystallized from methanol.

Yield: 1.3 g (33.2% of theory); m.p. 179–183° C.; $^{13}$C-NMR (DMSO-$d_6$; 300 MHz): δ=48.8 $CH_2N$; 67.1 $CH_2O$; 67.3 $CH_2O$.

The synthesis of the compounds of Examples 115 to 123 us carried out analogously to the procedure as in Example 114.

TABLE 10

Subst. 1-benzyl-3-alkyloxyindazol-5-amines

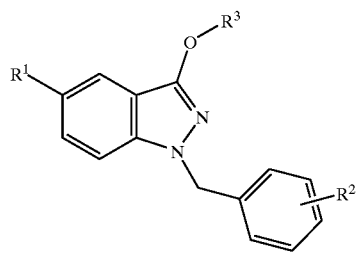

$R^2 = 3,4-Cl_2$

| Example | $R_1$ | $R_3$ | Yield (% of theory) | M.p. [° C.] | $^{13}$C-NMR (DMSO-$d_6$) N—$CH_2$/O—$CH_2$ |
|---|---|---|---|---|---|
| 115 | naphthalen-1-yl urea | $CH_2$-phenyl-O-(4-Cl) | 19 | 159–168 (MeOH) | 48.33/64.65; 65.35 |
| 116 | naphthalen-1-yl urea | $CH_2$-phenyl-O-(4-$NO_2$) | 6 | 178–188 (MeOH) | 48.37/65.29; 65.48 |

TABLE 10-continued

Subst. 1-benzyl-3-alkyloxyindazol-5-amines

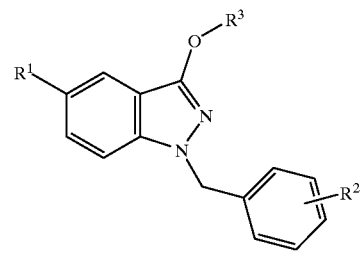

$R^2 = 3,4\text{-}Cl_2$

| Example | $R_1$ | $R_3$ | Yield (% of theory) | M.p. [° C.] | $^{13}C$-NMR (DMSO-$d_6$) N—CH$_2$/O—CH$_2$ |
|---|---|---|---|---|---|
| 117 | (1-naphthyl)NHC(O)NH— | —CH$_2$—C$_6$H$_4$—Cl (4-Cl) | 23 | 146–153 (MeOH) | 50.63/71.05 |
| 118 | (4-MeO-C$_6$H$_4$)NHC(O)NH— | —CH$_2$—C$_6$H$_4$—Cl (4-Cl) | 23 | 149–155 (MeOH) | 50.44/71.01 |
| 119 | (4-Cl-C$_6$H$_4$)NHC(O)NH— | —CH$_2$—C$_6$H$_4$—Cl (4-Cl) | 50 | 209–211 (BuOH) | 50.71/71.03 |

Formula XVI $R^2 = 2,4\text{-}Cl_2$

| Example | $R_1$ | $R_3$ | Yield (% of theory) | M.p. [° C.] | $^{13}C$-NMR (DMSO-$d_6$) N—CH$_2$/O—CH$_2$ |
|---|---|---|---|---|---|
| 120 | (1-naphthyl)NHC(O)NH— | —CH$_2$—O—C$_6$H$_4$—Cl (4-Cl) | 31 | 184–187 (dioxane) | 49.13/66.93; 67.82 |

-continued

Formula XVI
R² = 2,4-Cl₂

| Example | R₁ | R₃ | Yield (% of theory) | M.p. [° C.] | ¹³C-NMR (DMSO-d₆) N—CH₂/O—CH₂ |
|---|---|---|---|---|---|
| 121 | naphthyl-NH-C(O)-NH- | CH₂-O-C₆H₄-NO₂ | 33 | 179–183 (MeOH) | 48.87/67.16; 67.33 |
| 122 | naphthyl-NH-C(O)-NH- | CH₂-C(O)-C₆H₄-Cl | 26 | 185–187 (BuOH) | 49.00/71.01 |
| 123 | H₃C-O-C₆H₄-NH-C(O)-NH- | CH₂-C(O)-C₆H₄-Cl | 39 | 192–196 (MeCN) | 48.98/70.98 |

To determine the anti-asthmatic, anti-allergic, anti-inflammatory and/or immunomodulating properties of the compounds according to the invention, in-vitro and in-vivo investigations were carried out. The compounds according to the invention as in formula I are surprisingly distinguished by immunophilin binding and inhibit its peptidyl-prolyl cis-transisomerase (PPIase) activity. For the initial screening (10 μmol/l), the inhibition of human cyclophilin B in the PPIase test is determined.

Assay for the Determination of the Peptidylprolyl Isomerase (PPIase) Activity and Inhibition Method:

The PPIase activity is tested according to a globally customary enzyme test: G. Fischer, H. Bang, C. Mech, Biomed. Biochim. Acta 43 1101–1111; G. Fischer, H. Bang, A. Schellenberger, Biochim. Biophys. Acta 791 (1984), 87–97; D. H. Rich et al., J. Med. Chem. 38 (1995), 4164–4170.

The compounds of the general formula I according to the invention are preincubated at 4° C. for 15 minutes together with 10 nmol of Cyp B. The enzyme reaction is started using the test peptide Suc-Ala-Ala-Pro-Phe-Nan after addition of chymotrypsin and HEPES buffer. The extinction change at 390 nm is then monitored and evaluated. The photometrically determined extinction change results from two subreactions: a) the rapid chymotryptic cleavage of the transpeptide; b) the non-enzymatic cis-trans isomerization, which is catalysed by cyclophilins. The corresponding PPIase activities of the compounds of the general formula I according to the invention are shown in Table 11:

TABLE 11

| Example | Inhibition of the PPIase activity in [%] at 10 μM |
|---|---|
| 1 | 95 |
| 7 | 70 |
| 9 | 90 |
| 32 | 70 |
| 41 | 71 |
| 66 | 40 |
| 73 | 67 |
| 84 | 90 |
| 114 | 100 |
| 116 | 90 |
| 121 | 100 |

Inhibition of Late-phase Eosinophilia 24 h After Inhalational Ovalbumin Challenge in Actively Sensitized Guinea-pigs Method:

The inhibition of pulmonary eosinophil infiltration by the substances is tested in an in-vivo test on male Dunkin-Hartley guinea-pigs (200–250 g) sensitized against ovalbumin (OVA). The sensitization is carried out by means of two intraperitoneal injections of a suspension of 20 μg of OVA together with 20 mg of aluminium hydroxide as an adjuvant in 0.5 ml of physiological saline solution per animal on two successive days. 14 days after the second injection, the animals are pretreated with mepyramine maleate (10 mg/kg i.p.) in order to protect them from anaphylactic death. 30 minutes later, the animals are exposed for 30 sec in a plastic box to an OVA aerosol (0.5 mg/ml) which is generated by a nebulizer driven by compressed air (19.6 kPa) (allergen challenge). Control animals are nebulized with physiological saline solution. 24 hours after the challenge, the animals are anaesthetized with an overdose of ethylurethane (1.5 g/kg of body weight i.p.) and a bronchoalveolar lavage (BAL) is carried out with 2×5 ml of physiological saline solution. The BAL fluid is collected, centrifuged at 300 rpm for 10 min and the cell pellet is then resuspended in 1 ml of physiological saline solution. The eosinophils are stained using the Becton-Dickinson test kit (N. 5877) for eosinophils and counted in a Neubauer chamber. 2 control groups (nebulization with physiological saline solution and nebulization with OVA solution) are additionally included in each test.

The percentage inhibition of the eosinophilia of the test group treated with substance is calculated according to the following formula:

(A–C)–(B–C)/(A–C)×100=% inhibition

The test substances are administered intraperitoneally or orally as a suspension in 10% polyethylene glycol 300 and 0.5% strength 5-hydroxyethylcellulose 2 hours before allergen challenge. The control groups are treated with the vehicle according to the administration form of the test substance. The number of animals per control and test group is 3–10. The results are listed in the following table:

TABLE 12

| Example | Dose [mg/kg] | Administration | Eosinophil million/animal x̄ ± s | | | Inhibition [%] |
| --- | --- | --- | --- | --- | --- | --- |
| | | | A | B | C | |
| 1 | 10 | i.p. –2 h | 2.11 ± 1.05 | 1.23 ± 0.38 | 0.67 ± 0.23 | 61 |
| | 30 | p.o. –2 h | 3.49 ± 1.47 | 1.75 ± 1.86 | 0.83 ± 0.30 | 65 |
| 8 | 10 | i.p. –2 h | 2.46 ± 1.08 | 1.84 ± 0.94 | 0.97 ± 0.47 | 41 |
| 32 | 10 | i.p. –2 h | 1.93 ± 0.75 | 0.86 ± 0.49 | 0.66 ± 0.12 | 85 |
| 91 | 10 | i.p. –2 h | 2.89 ± 1.66 | 1.16 ± 0.65 | 0.47 ± 0.24 | 71 |
| 99 | 10 | i.p. –2 h | 1.93 ± 0.75 | 1.35 ± 0.67 | 0.66 ± 0.12 | 46 |
| | 30 | p.o. –2 h | 1.81 ± 0.23 | 1.33 ± 0.23 | 0.33 ± 0.08 | 33 |
| 107 | 10 | i.p. –2 h | 2.46 ± 1.08 | 1.44 ± 0.92 | 0.97 ± 0.47 | 68 |
| 114 | 10 | i.p. –2 h | 1.93 ± 0.75 | 1.19 ± 0.43 | 0.66 ± 0.12 | 58 |

A = Eosinophils in the control group with OVA challenge and vehicle
B = Eosinophils in the group treated with substance with OVA challenge
C = Eosinophils in the control group with 0.9% strength NaCl challenge and vehicle
x̄ = Average value
s = Standard deviation The compounds according to the invention are thus particularly suitable for the production of medicaments for the treatment of diseases which are connected with the suppression of immunological processes.

What is claimed is:

1. 1,5- and 3-O-substituted 1H-indazoles of formula (I)

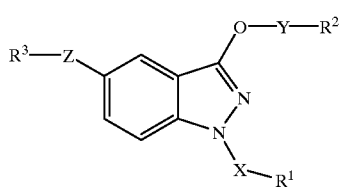

(I)

wherein

X is —SO$_2$—, —SO—, —(CH$_2$)$_p$—, —(CH$_2$)$_p$—O—, —(CH$_2$)$_p$—(C=O)—, —(CH$_2$)$_p$—(C=O)—NH—, —(CH$_2$)$_p$—CHOH—, —CHOH—(CH$_2$)$_p$—, —(CH$_2$)$_p$—CH=CH—, —CH=CH—(CH$_2$)$_p$—,

Y is —(CH$_2$)$_p$—, —(CH$_2$)$_p$—O—, —(CH$_2$)$_p$—(C=O)—, —(CH$_2$)$_p$—(C=O)—NH—, —(CH$_2$)$_p$—(C=O)—NH—(CH$_2$)$_p$—, —(CH$_2$)$_p$—CHOH—, —CHOH—(CH$_2$)$_p$—, —(CH$_2$)$_p$—CH=CH—, —CH=CH—(CH$_2$)$_p$—,

Z is —O—, —S—, —SO—, —SO$_2$—NH, —O—(CH$_2$)$_p$—, —NH—(C=O)—, —NH—(C=O)—NH—, —NH—(C=O)—O—, —NH—CH$_2$—(C=O)— and —NH—(C=O)—CH$_2$—, P is a cardinal number from 1 to 4, R$^1$, R$^2$ and R$^3$ are the same or different, and are mono-, bi- or tricyclic saturated or mono- or polyunsaturated carbocycles having from 5 to 14 ring members, or mono-, bi- or tricyclic saturated or mono- or polyunsaturated heterocycles having from 5 to 15 ring members and from 1 to 6 heteroatoms, wherein the carbocycles and the heterocycles can be mono- or polysubstituted by —C$_{1-6}$-alkyl, —O—C$_{1-6}$-alkyl, —O—C$_{3-7}$-cycloalkyl, mono-, bi- or tricyclic saturated or mono- or polyunsaturated carbocycles having from 3 to 14 ring members, mono-, bi- or tricyclic saturated or mono- or polyunsaturated heterocycles having from 5 to 15 ring members and from 1 to 6 heteroatoms, R$^1$ can also be H provided that X is not CH$_2$), and R$^3$—Z can also be NO$_2$ and their pharmaceutically acceptable salts, but excluding if Y=—(CH$_2$)$_p$—(C=O)—, —(CH$_2$)$_p$—(C=O)—NH—, then R$^2$ is not pyridine, piperazine, pyrimidine, tetrahydropyridine; and when Z is —NH—(C=O)—, —NH—(C=O)—NH—, —NH—(C=O)—O—, —NH—(C=O)—CH$_2$— and R$^1$ is at the same time phenyl, monosubstituted or polysubstituted by —COOH, —COOC$_{1-6}$-alkyl, —(CH$_2$)$_p$—COOH, —(CH$_2$)$_p$—COOC$_{1-6}$-alkyl, —CONHC$_{1-6}$-alkyl, —CONHC$_{6-14}$-aryl, —CONHSO$_2$C$_{1-6}$-alkyl, —CONHSO$_2$C$_{6-14}$-aryl, 1H-tetrazol-5-yl, then R$^2$ must not be phenyl, monosubstituted or polysubstituted by CN, halogen, C$_{1-4}$-alkyl, C$_{1-4}$-alkyloxy, CF$_3$; and if R$^3$—Z is NO$_2$, then R$^1$—X is not benzyl or 4-methoxybenzyl and R$^2$—Y is not benzyl or 2-picolyl at the same time.

2. The compounds of claim 1, wherein in R$^1$, R$^2$, and R$^3$ said carbocycles of 4 to 14 ring members are one or more of phenyl, naphthyl, anthranyl, and fluorenyl residue; and wherein in $R^1$, $R^2$, and $R^3$ said heteroatoms are N, O, or S; and wherein said heteroatoms mono- or polysubstituting said carbo-cycles and said heterocycles are N, O and S, —F, —Cl, —Br, —I, —OH, —SH, —$NO_2$, —$NH_2$, —$NHC_{1-6}$-alkyl, —$N(C_{1-6}$-alkyl$)_2$, —$NHC_{6-14}$-aryl, —$N(C_{6-14}$-aryl$)_2$, —$N(C_{1-6}$-alkyl$)$—$(C_{6-14}$-aryl$)$, —$NHCOC_{1-6}$-alkyl, —$NHCOC_{6-14}$-aryl, —$CONHC_{1-6}$-alkyl, —$CONHC_{6-14}$-aryl, —$CONHSO_2C_{1-6}$-alkyl, —$CONHSO_2C_{6-14}$-aryl, —CN, —$(CO)C_{1-6}$-alkyl, —$(CS)C_{1-6}$-alkyl, —COOH, —$COOC_{1-6}$-alkyl, —O—$C_{6-14}$-aryl, —O—$(CO)C_{1-6}$-alkyl, —O—$(CO)C_{6-14}$-aryl, benzyl, benzyloxy, —S—$C_{1-6}$-alkyl, —S—$C_{6-14}$-aryl, —$CF_3$, —$(CH_2)_p$—COOH, —$(CH_2)_p$—$COOC_{1-6}$-alkyl, —$SO_2$—$C_{1-6}$-alkyl, or —$SO_2$—$C_{6-14}$-aryl.

3. The compounds of claim 1, wherein when $R^1$, $R^2$, and/or $R^3$ is a heterocycle, are independently of each other thiophenyl, pyridinyl, isoxazolyl, benzimicdazolyl, benzo[1,3]dioxolyl, pyrimidinyl, quinolyl, quinazolinyl, morpholinyl, pyrrolydinyl, pyrrolyl, benz[1,2,4]oxadiazolyl, or benzothiazolyl residues.

4. A compound of claim 1, being

3-[2-(2-bromo-4,6-difluorophenoxy)ethoxy]-5-methoxy-1-(toluene-4-sulfonyl)-1H-indazole;

5-methoxy-1-(toluene-4-sulfonyl)-3-[5-(3-trifluoromethylphenyl)-1,2,4-oxadiazol-3-ylmethoxy]-1H-indazole;

6-{2-[5-methoxy-1-(toluene-4-sulfonyl)-1H-indazol-3-yloxy]acetyl}-3,4-dihydro-1H-quinolin-2-one;

N-(2,4-ditluorophenyl)-2-[5-methoxy-1-(toluene-4-sulfonyl)-1H-indazol-3-yloxy]acetamide;

3-(6-chlorobenzo[1,3]dioxol-5-ylmethoxy)-5-methoxy-1-(3-nitrobenzyl)-1H-indazole;

3-[3-(4-fluorophenyl)-propoxy]-5-nitro-1-(3-nitrobenzyl)-1H-indazole;

3-[3-(6-chlorobenzo[1,3]dioxol-5-ylmethoxy)-5-methoxy-indazol-1-ylmethyl]phenylamine;

1-(4-fluorobenzyl)-5-methoxy-3-[2-(4-nitrophenoxy)ethoxy]-1H-indazole;

3-[2-(2-bromo-4,6-difluorophenoxy)ethoxy]-5-methoxy-1-[2-(4-nitrophenoxy)ethyl]-1H-indazole;

3-[2-(2-bromo-4,6-difluorophenoxy)ethoxy]-1-[3,4-dichlorobenzyl]-5-methylthio-1H-indazole; or 1-{1-(2,4-dichlorobenzyl)-3-[2-(4-nitrophenoxy)ethoxy]-1H-indazol-5-yl}-3-naphthalen-1-ylurea.

5. The pharmaceutically acceptable salts of claim 1, obtained by (i) neutralization of the bases with inorganic or organic bases, (ii) neutralization of the acids with inorganic or organic bases, or (iii) quaternization of a teriary amine to give a quaternary ammonium salt.

6. A process for the treatment of diseases mediated by PPIase, which comprises administering to a patient in need therefor a pharmaceutical composition containing as active ingredient the compound or salt of claim 1.

7. An immunomodulating, antiinflammatory, antiallergic process which comprises administering to a patient in need therefor a pharmaceutical composition containing as active ingredient the compound or salt of claim 1.

8. A process for preparing a compound of claim 1, which comprises (a) when X is —$SO_2$—, or —SO— by reacting a 1H-indazolyl-3-yl sulfonate of formula

(II)

in the presence of a base and in the optional presence of a diluent to provide a compound of formula (III)

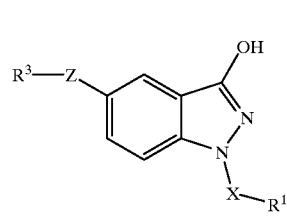

(III)

where $R^1$, $R^3$, X and Z have the same meaning, and reacting a 1H-indazol-3-yl sulfonate of formula (II), or a 1-sulfonylindazole of formula (III), optionally in the presence of a base, and in the optional presence of a diluent, with a compound of the formula Hal-Y-$R^2$, where $R^1$, $R^2$, $R^3$, X, Y and Z have the same meaning, and Hal is a halogen atom to provide a compound of formula (I); or (b) when X is —$(CH_2)_p$—, —$(CH_2)_p$—O—, —$(CH_2)_p$—(C=O)—, —$(CH_2)_p$—(C=O)—NH—, —$(CH_2)_p$—CHOH—, —CHOH—$(CH_2)_p$—, —$(CH_2)_p$—CH=CH—, —CH=CH—$(CH_2)_p$—, by reacting compounds of formula (III), the optional presence of a base, and in the optional presence of a diluent, with a compound of the formula Hal-Y-$R^2$, where $R^1$, $R^2$, $R^3$, X, Y and Z have the same meanings, and Hal is a halogen atom, to provide a compound of formula (I); or (c) where the compound of formula (III) is present as the tautomeric form of the compound of formula (IV)

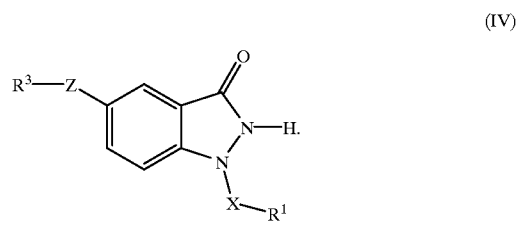

(IV)

9. The process of claim 8, wherein in said the optional base is sodium hydride, and said optional diluent is dimethyl sulfoxide.

10. A pharmaceutical composition containing at least one compound of claim 1 as active ingredient, together with a pharmaceutically acceptable carrier and/or diluent or auxiliary.

11. The pharmaceutical composition of claim 10, when it is in the form of a coated or uncoated tablet, capsule, aerosol, powder formulation, patch, solution, ampoule, or suppository.

* * * * *